(12) United States Patent
Weinberg

(10) Patent No.: US 11,357,997 B2
(45) Date of Patent: Jun. 14, 2022

(54) EQUIPMENT AND METHODOLGIES FOR NON-INVASIVE TREATMENT FOR ADDICTION

(71) Applicant: Weinberg Medical Physics, Inc., North Bethesda, MD (US)

(72) Inventor: Irving N. Weinberg, North Bethesda, MD (US)

(73) Assignee: WEINBERG MEDICAL PHYSICS INC., North Besthesda, MD (US)

(\*) Notice: Subject to any disclaimer, the term of this patent is extended or adjusted under 35 U.S.C. 154(b) by 659 days.

(21) Appl. No.: 16/120,974

(22) Filed: Sep. 4, 2018

(65) Prior Publication Data

US 2019/0070427 A1 Mar. 7, 2019

Related U.S. Application Data

(60) Provisional application No. 62/553,488, filed on Sep. 1, 2017.

(51) Int. Cl.
| | | |
|---|---|---|
| *A61N 2/00* | (2006.01) | |
| *A61M 21/00* | (2006.01) | |
| *A61M 15/08* | (2006.01) | |
| *A61N 2/12* | (2006.01) | |
| *G01R 33/38* | (2006.01) | |
| *A61B 5/0515* | (2021.01) | |
| *A61B 34/20* | (2016.01) | |
| *A61B 34/00* | (2016.01) | |
| *A61B 5/055* | (2006.01) | |

(52) U.S. Cl.
CPC ............ *A61N 2/006* (2013.01); *A61M 15/08* (2013.01); *A61M 21/00* (2013.01); *A61N 2/12* (2013.01); *A61B 5/055* (2013.01); *A61B 5/0515* (2013.01); *A61B 34/73* (2016.02); *A61B 2034/2051* (2016.02); *A61M 2021/0022* (2013.01); *A61M 2021/0055* (2013.01); *A61M 2205/0272* (2013.01); *G01R 33/3808* (2013.01)

(58) Field of Classification Search
CPC ....... A61M 37/00; A61M 15/08; A61N 2/006; A61N 2/12; A61B 34/73; A61B 5/055
See application file for complete search history.

(56) References Cited

U.S. PATENT DOCUMENTS

| | | | | |
|---|---|---|---|---|
| 2007/0299550 | A1* | 12/2007 | Nishijima | A61M 37/00 700/61 |
| 2010/0303716 | A1* | 12/2010 | Jin | A61M 37/0092 424/1.11 |
| 2013/0046169 | A1* | 2/2013 | Weinberg | A61N 2/02 600/411 |
| 2014/0042831 | A1* | 2/2014 | DiLuciano | B60L 3/0092 307/328 |
| 2018/0368726 | A1* | 12/2018 | Weinberg | A61N 1/0534 |

\* cited by examiner

*Primary Examiner* — Samuel G Gilbert
(74) *Attorney, Agent, or Firm* — Barnes & Thornburg LLP

(57) ABSTRACT

Methodologies and mechanisms are provided for introducing one or more magnetizable particles introduced non-invasively into one or more body structures containing nervous tissue in a subject, directing, guiding, transporting, focusing and/or concentrating the one or more particles using at least one image-guidance component in proximity to the one or more body structures which can direct the one or more particles within the one or more body structures, and modulating, using at least one activation component, the one or more particles to modulate neuronal function in the one or more body structures of the subject.

14 Claims, 3 Drawing Sheets

EQUIPMENT AND METHODOLGIES FOR NON-INVASIVE TREATMENT FOR ADDICTION

CROSS REFERENCE AND PRIORITY CLAIM

This patent application claims priority to U.S. Provisional Application Provisional Patent Application No. Patent Application Ser. No. 62/533,488, "NONINVASIVE TREATMENT FOR ADDITION," filed Sep. 1, 2017, the disclosure of which being incorporated herein by reference in its entirety.

FIELD

Disclosed embodiments pertain to therapy of subjects, or patients, with addictive and other disorders.

BACKGROUND

It is known that addictive and other neurological disorders of a subject or patient can be treated with invasive deep brain stimulation of specific locations in the brain, as described by J Kuhn et al in the 2014 publication in the journal Molecular Psychiatry entitled "Deep brain stimulation of the nucleus accumbens and its usefulness in severe opioid addiction" (incorporated herein by reference).

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

Disclosed embodiments provide a non-invasive method and associated equipment for accomplishing deep brain stimulation of subjects similar results and additional advantages.

In accordance with disclosed embodiments, one or more magnetizable particles may be introduced non-invasively into one or more body structures containing nervous tissue within a subject.

In accordance with disclosed embodiments, at least one image-guidance component located in proximity to the one or more body structures may be used to direct, transport, concentrate and/or focus the one or more particles within the one or more body structures within a subject.

In accordance with disclosed embodiment, at least one activation component may be used to cause the one or more particles to modulate neuronal function in the one or more body structures within a subject.

BRIEF DESCRIPTION OF THE FIGURES

The detailed description particularly refers to the accompanying figures in which.

DETAILED DESCRIPTION

The description of specific embodiments is not intended to be limiting of the present invention. To the contrary, those skilled in the art should appreciate that there are numerous variations and equivalents that may be employed without departing from the scope of the present invention. Those equivalents and variations are intended to be encompassed by the present invention.

In the following description of various invention embodiments, reference is made to the accompanying drawings, which form a part hereof, and in which is shown, by way of illustration, various embodiments in which the invention may be practiced. It is to be understood that other embodiments may be utilized and structural and functional modifications may be made without departing from the scope and spirit of the present invention.

As explained above, in accordance with at least one disclosed embodiment, instrumentation and methodologies are provided that enable non-invasive mechanisms and methodologies for accomplishing deep brain stimulation.

Conventionally, it is known that objects placed in certain biological structures in the brain or other parts of the central or peripheral nervous system or in nerves may have an effect on such biological structures. However, it should be understood that, in some cases, for example as reported in the 2014 scientific articles by A E Ross, et al in the Journal of Neurochemistry entitled "Mechanical stimulation evokes rapid increases in extracellular adenosine concentration in the prefrontal cortex" (incorporated by reference herein), mechanical motion of an object can modulate the neuronal activity in nearby structures.

The present inventors have shown that it was possible to apply changing magnetic fields external to an animal with an aim of stimulating neurons in the animal, in the presentation by A Nacev, et al entitled, "Neurostimulation using mechanical motion of magnetic particles wiggled by external oscillating magnetic gradients," described in the Proceedings of the Eighth International IEEE EMBS Neural Engineering Conference held in Shanghai in 2017 (incorporated by reference in its entirety).

Disclosed embodiments provide equipment and methodologies for treating addiction and other disorders of the nervous system with non-invasive means. The apparatus includes a means of entering the nervous system non-invasively, for example via intra-nasal administration as in FIG. 1, where one or more magnetizable particles are introduced into the nose possibly via an optional applicator with an nozzle or some other type of applicator.

Figure 1:
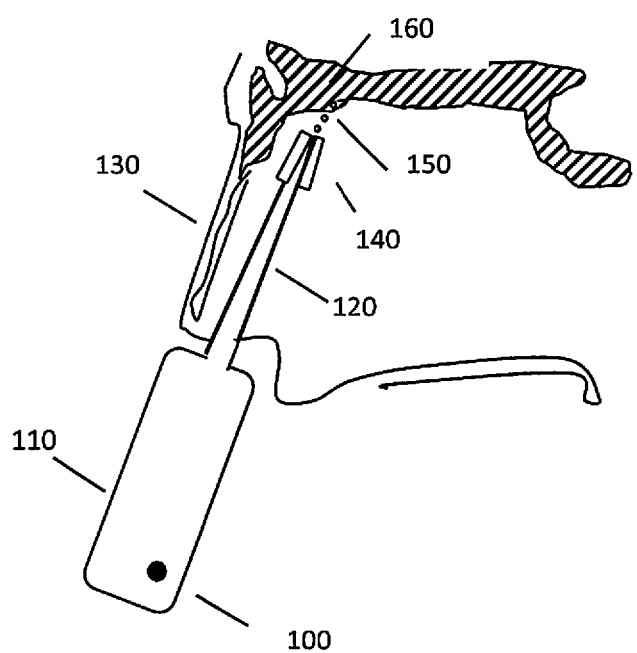
FIG. 1 illustrates an embodiment of the invention, wherein administration of one or more magnetizable particles are administered initially from a unit dose container and applicator into the nose of a subject who may have an addiction disorder or some other neurological or psychological or pain or other disorder.

More specifically, FIG. 1 illustrates a disclosed embodiment wherein one or more magnetizable particles 100 may be administered initially from a unit dose container 110 and applicator 120 into the nose 130 of a subject who may have an addiction disorder or some other neurological or psychological or pain or other disorder. Applicator 120 may have a nozzle 140 through which particles may be instilled under pressure in the nose, with penetration of particles 150 via pores in the cribriform plate 160 and into the brain and cranium.

Particles 150 are shown traversing pores in the cribriform plate 160 in order to enter the cranial cavity. Particles 100 may be pulled into the nose and/or across the cribriform plate 160 through application of a magnetic field as shown in FIG. 2.

In an alternative embodiment, one or more particles 100 may be introduced into the body via another non-invasive means, for example intra-venously or by inhalation.

Figure 2:
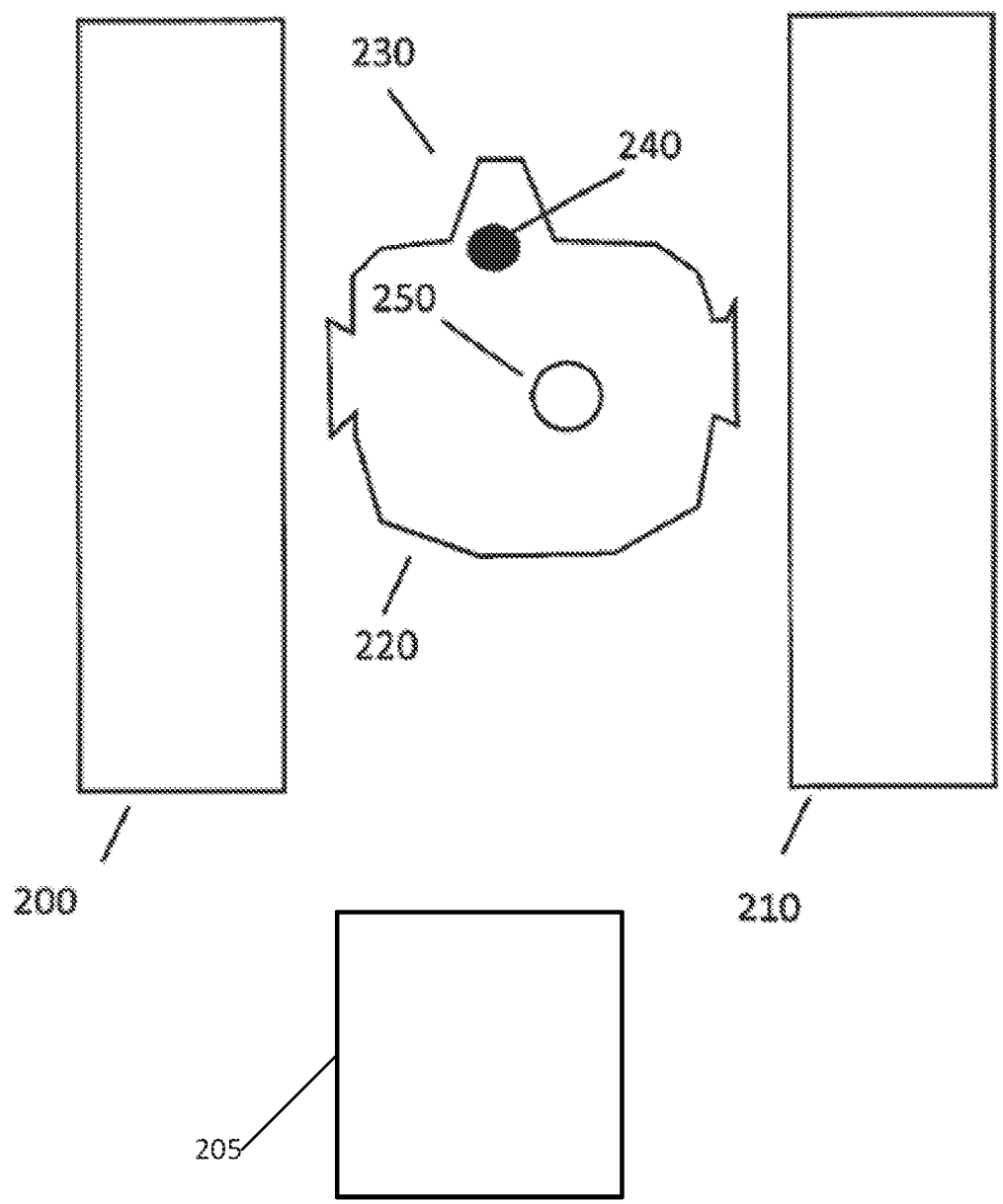
FIG. 2 is an explanatory illustration of how a magnetic field is applied to the subject, wherein image-guidance components of a system are used to apply such a magnetic field under imaging guidance.

FIG. 2 shows image-guidance components 200 and 210 of a system to apply such a magnetic field under imaging guidance. Image-guidance components 200 and 210 may include permanent magnets, electromagnets, antennas or electropermanent magnets, as taught in It should be understood that the apparatus 200 for applying magnetic fields for imaging and/or manipulation may use electropermanent magnets, as taught by Irving Weinberg in US Pat. Pub. 20170227617, corresponding to U.S. patent application Ser. No. 15/427,426, entitled "METHOD AND APPARATUS FOR MANIPULATING ELECTROPERMANENT MAGNETS FOR MAGNETIC RESONANCE IMAGING AND IMAGE GUIDED THERAPY," incorporated herein by reference. Such electropermanent magnets may at one or more times create a magnetic field configuration for imaging of a subject's body part. It should be understood that the imaging capability may be through magnetic resonance imaging methods.

It should be understood that "image-guided" and "image-guidance" for the purposes of this disclosure means the use of magnetic resonance imaging of structures and of anatomy to assist in delivery of one or more particles to a structure, and that "image-guided magnetic delivery" means the use of image guidance with magnetic forces applied to the one or more particles during delivery.

In FIG. 2, image-guidance components 200 and 210 are shown on both sides of human head 220, although it is understood that other system configurations might employ a single-sided MRI on one side of head 220 or an annular MRI or some other configuration near human or non-human animal head 220. One or more particles 240, corresponding to the same object 100 in FIG. 1, may be guided magnetically under imaging guidance to or near one or more pre-determined biological structures 250 in the human or non-human animal head 220.

Structure 250 may be implemented using or as part of a nucleus accumbens. It should be understood that structure 250 may be in the brain, medulla, or other sections of the central or peripheral nervous system. Particle 240 may be activated by image-guidance component 200 or 210, such activation possibly including electromagnetic or electrical or magnetic fields created by image-guidance component 200 or 210 in addition to image-guidance. Such activation may include motion, so that one or more neurons in structure 250 is stimulated or modulated or otherwise affected by such motion.

As shown, the head 220 of FIG. 2, having received particles 100, 240 via the nose 130 or other non-invasive means, is in proximity to magnetic or electromagnetic image-guidance components 200 and/or 210. It should be understood that image-guidance components 200 may be near the head 220 during intra-nasal administration (as in FIG. 1 in order to assist in propelling particles 100, 240 via the pores in the cribriform plate 160. It should be understood that such transport may be along neurons or around neurons in the cribriform plate. Image-guidance components 200 and/or 201 are representative of components of an image-guided propulsion system capable of visualizing both particles 100 as well as anatomic information concerning structures such as 250 in the head 220.

In accordance with at least one embodiment, such an image-guided propulsion system may be implemented as, include or work in conjunction with a Magnetic Resonance Imaging (MRI) utilizing electropermanent magnets.

In accordance with at least one embodiment, electromagnetic coils or other magnetic image-guidance components of such an image-guided propulsion system may generate magnetic fields that can concentrate or otherwise propel particles 240 to the location of or near structure 250. The image-guided propulsion process may be as described in U.S. Pat. No. 9,380,959 by Irving Weinberg et al, entitled "MRI-GUIDED NANOPARTICLE CANCER THERAPY APPARATUS AND METHODOLOGY" (incorporated by reference in its entirety) in which sets of magnetic pulses are applied to the particle or particles. The image-guided propulsion system may also mechanically vibrate the particle or particles 240 once in place in or near structure 240 or along the way to such structure, to verify an intended biological effect, for example, cessation of addictive symptoms.

It should be understood that techniques for imaging particles in the body of the subject may assist in image-guided delivery, as taught by Alek Nacev in US Patent Publication 20170139024 corresponding to U.S. patent application Ser. No. 15/352,164, entitled "METHOD AND APPARATUS FOR HIGH SLEW RATE SINGLE POINT MAGNETIC RESONANCE IMAGING OF MAGNETIZABLE NANOPARTICLES" (incorporated herein by reference.

Figure 3:
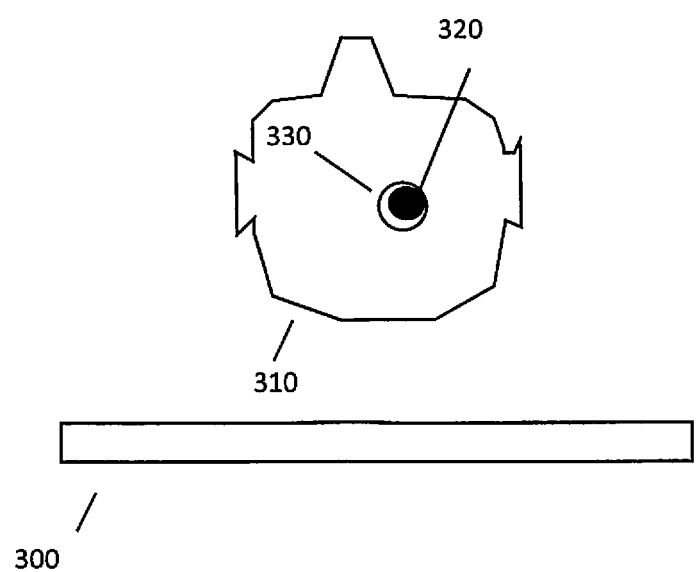
FIG. 3 illustrates a magnet or electromagnet activation component disposed in proximity to a subject's head corresponding to that illustrated in FIG. 2.

FIG. 3 illustrates an example of a magnet or electromagnet activation component 300 disposed in proximity to a human or non-human animal head 310, such head corresponding to 220 in FIG. 2. One or more particles 320, corresponding to 240 in FIGS. 2 and 100 in FIG. 1, is shown within structure 330, corresponding to part 250 in FIG. 2.

Activation component 300 may emanate magnetic or electromagnetic fields that activate one or more particles 320 and stimulate or otherwise modulate neurological activity of neurons in structure 330.

It should be understood that activation component 300 may be located in an office, or may be wearable by the subject, and may contain a power source, and may be addressed or otherwise contacted by wireless or radio signals from a computer or cell phone or other electronic device. Thus, in accordance with at least one embodiment, the subject may be a patient being treated once he or she has left the vicinity of the image-guided propulsion system, as shown schematically in FIG. 3.

Accordingly, one or more particles 320, having previously been placed in or near biological structure 330, may be activated by activation component 300. Activation component 300 may be in an office, portable, wearable, or may be attached to a cellular or smart phone, or may be held by a patient, or may be in a structure (for example, a bed or chair) that the subject rests upon.

Activation component 300 may be, for example, less than 10 kilogram in weight, or less than one kilogram in weight. Activation component 300 may emanate magnetic or electromagnetic radiation that causes particle or particles 320 to have an effect on one or more neurons in the biological structure 330. For example, the particles 320 may vibrate in order to stimulate the neurons in the structure 330.

It should be understood that activation component 300 may have its own power source or may be connected to a power source by a wire (not shown) or wireless connection. It should also be understood that the pulses or emanations from activation component 300 may be fired selectively in order to activate structures in one location and not in another location. Such selectivity may be implemented, for example, by having particles of one shape that are tuned to a pulse from activation component 300, such tuning being mechanical or electrical or magnetic or a combination of such methods.

It should be understood that activation component 300 may be composed of one or more smaller components and/or coils. It should also be understood that activation component 300 may include, be included in or be coupled to and/or activated by a computer, such that the activation only occurs upon receipt by the computer of a secret code, which may not be known by the subject. Further, it should be understood that the activation component 300 may be included in the same equipment as the image-guided propulsion system discussed above.

It should be understood that one or more magnetic fields applied by image-guided propulsion system and activation components 200, 210, 300 to a tissue or body part may be so rapidly applied so as not to cause unpleasant nerve stimulation, as taught by Irving Weinberg in issued U.S. Pat. No. 8,154,286, entitled "APPARATUS AND METHOD FOR DECREASING BIO-EFFECTS OF MAGNETIC FIELDS" (incorporated by reference) and patent applications related by priority claim, by Irving Weinberg, which are all incorporated herein by reference.

It should be understood that the term "subject" refers to and includes humans and other animals, whether they be alive or once-living. Similarly, the term "body part or other structure" may mean a tissue-containing structure in a living or once-living organism such as a human or other animal.

Likewise, it should be understood that the term "structure" may mean a tissue-containing structure in a living or once-living organism such as a human or other non-human animal. It should be understood that the terms "neural structure" and "neuronal structure" mean a structure containing neurons or nerves. It should be understood that the term "head" may be generalized to any neuronal structure in a human or non-human animal.

It should be understood that the term "magnetizable particle" may refer to a particle made of material that exhibits magnetic or electric properties after or during exposure to a magnetic field. It should be understood that the term "particle" means an object smaller than 1 mm, 100 micron, 10 microns, 1 micron, 0.1 microns, or 0.01 microns in the smallest diameter.

It should be understood that particle 100 may be constructed so as to degrade after a pre-determined period of time, for example a month or several months or a year, corresponding to the expected treatment period. It should be understood that such degradation may be accelerated through appropriate activation of the particle 100 by activation or image-guidance components 200, 210, or 300, for example through motion of the particle. It should be understood that the term "degrade" means that no significant residual material from the particle is present in the structure at the end of the degradation period. The term "significant" is used herein to mean without harm to the structure.

It should be understood that the terms "neuron" and "neuronal" may include reference to neurons, nerves or nervous tissue of any type.

The terms "near" and "proximity" may be less than one meter, less than 10 meters, or less than 100 meters. It should be understood that a computer is generally connected to components 200, 210, or 300 for collection, reconstruction, display, and/or interpretation of data from the at least component.

The term "neurological disorder" is used herein to include addiction disorders, psychiatric disorders, pain, or other neurological disorders of the central or peripheral nervous systems or of any structure containing nervous tissues. The term "patient" is used herein to mean a human person or non-human animal with a neurological disorder.

The term "noninvasive" is used herein to include intra-nasal or intra-venous or topical or oral methods of introducing a material into the body.

The terms "modulate", "neuromodulate", "modulation", and "neuromodulation" are understood to mean stimulation or suppression or any change of neuronal function. It should be understood that suppression can be implemented through repeated stimulation.

In accordance with at least one embodiment, a method is provided for treating patients with addictive and psychiatric and neurological disorders. Such a method includes the introduction of one or more particles non-invasively into the subject's body, propelling the one or more particles into one or more structures in nervous tissue in the subject's body under imaging guidance by one or more image-guidance components, and then activating neurons in such nervous tissue structures (possibly as an outpatient) with image-guidance components or with an activation component.

In accordance with at least one embodiment, one or more particles may dissolve or be otherwise degraded so as not to remain permanently in the subject's body.

In accordance with at least one embodiment, image-guidance and/or activation components may be activated only upon receipt of the components by a code sent by a computer or entered manually. Such a code may be one which the subject is not aware of, as this may be useful for therapeutic purposes.

It should be understood that the sequence and magnitude of the activation sequence of the particle in structure may vary from subject to subject, and within each subject over a period of time, according to therapeutic purposes.

It should be understood that various connections are set forth between elements in the following description; however, these connections in general, and, unless otherwise specified, may be either direct or indirect, either permanent or transitory, and either dedicated or shared, and that this specification is not intended to be limiting in this respect.

While this invention has been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

Additionally, it should be understood that the functionality described in connection with various described components of various invention embodiments may be combined or separated from one another in such a way that the architecture of the invention is somewhat different than what is expressly disclosed herein. Moreover, it should be understood that, unless otherwise specified, there is no essential requirement that methodology operations be performed in the illustrated order; therefore, one of ordinary skill in the art would recognize that some operations may be performed in one or more alternative order and/or simultaneously.

Various components of the invention may be provided in alternative combinations operated by, under the control of or on the behalf of various different entities or individuals.

Further, it should be understood that, in accordance with at least one embodiment of the invention, system components may be implemented together or separately and there may be one or more of any or all of the disclosed system components. Further, system components may be either dedicated systems or such functionality may be implemented as virtual systems implemented on general purpose equipment via software implementations.

It should be understood that components disclosed herein may be used in conjunction with, as described above, other components, for example a computer processor. In addition, the disclosed apparatus may include, utilize or be used in conjunction with a power supply and/or coils for generating magnetic and/or electromagnetic fields, in order to generate an electrical field. Thus, although not shown in detail herein, it should be understood that the disclosed embodiments may be used in conjunction with a support structure that may hold coils for exciting materials, wherein the support structure includes coils used to apply the electric field as well as, optionally, an imaging system to enable positioning and/or monitoring of the excited materials. Moreover, it should be understood that an associated display system is not shown but should be understood to be present in order to view images produced by the imaging system.

It should be understood that the operations explained herein may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors 205 programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control and cooperation of the above-described components may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments. Such alternative storage devices should be considered equivalents.

While certain illustrative embodiments have been described, it is evident that many alternatives, modifications, permutations and variations will become apparent to those skilled in the art in light of the foregoing description. Accordingly, the various embodiments of, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

What is claimed:

1. A method of treating a patient with a neurological disorder with noninvasive administration of one or more magnetizable particles, wherein the method comprises:
    performing image-guided magnetic delivery of the one or more magnetizable particles to a neural structure of a subject; and
    modulating the neural structure with at least one activation component so as to treat the neurological disorder.

2. The method of claim 1, wherein the neurological disorder is an addiction disorder.

3. The method of claim 1, wherein the modulation is activated by an authorization code that is not known to the subject.

4. The method of claim 1, wherein neuromodulation is implemented by moving the one or more magnetizable particles in the neural structure.

5. The method of claim 1, wherein the one or more magnetizable particles degrade in less than one month.

6. The method of claim 1, wherein the one or more magnetizable particles degrade in less than one year.

7. The method of claim 1, wherein the at least one activation component weighs less than 10 kilograms.

8. The method of claim 1, wherein the image-guided magnetic delivery of the one or more magnetizable particles to the subject's neural structure is performed using at least one image-guidance component positioned in proximity to the neural structure within the subject, wherein the at least one image-guidance component is configured to direct the one or more magnetizable particles within the one or more body structures.

9. The method of claim 8, wherein the at least one image-guidance component comprises an MRI system that includes at least one magnetic coil.

10. The method of claim 8, wherein the MRI system is a single-sided MRI system.

11. The method of claim 8, wherein the MRI system includes a plurality of electropermanent sections.

12. The method of claim 8, wherein the MRI system generates pulse sequences wherein the MRI has pulse sequences whose rise-time, fall-time, or duration are less than 10 microseconds long.

13. The method of claim 8, wherein the MRI system includes at least one magnetic coil generates a magnetic field that rises or falls in such short a time as not to cause nerve stimulation of the subject.

14. The method of claim 13, wherein the at least one magnetic coil generates a magnetic field that rises or falls in less than 10 microseconds.

\* \* \* \* \*